United States Patent [19]

Abiuso et al.

[11] Patent Number: 5,324,271
[45] Date of Patent: Jun. 28, 1994

[54] DOUBLE SEAL HEMOSTASIS CONNECTOR

[75] Inventors: Christopher L. Abiuso; Andrea T. Slater, both of Pembroke Pines, Fla.

[73] Assignee: Cordis Corporation, Miami Lakes, Fla.

[21] Appl. No.: 72,186

[22] Filed: Jun. 4, 1993

[51] Int. Cl.⁵ .............................................. A61M 5/31
[52] U.S. Cl. .................................... 604/167; 604/283
[58] Field of Search ............... 604/283, 164, 167, 169, 604/243, 256, 280, 284

[56] References Cited

U.S. PATENT DOCUMENTS

| | | | |
|---|---|---|---|
| 5,108,380 | 4/1992 | Herlitze et al. | 604/283 |
| 5,167,636 | 12/1992 | Clemenet | 604/167 |
| 5,205,831 | 4/1993 | Ryan et al. | 604/167 |

Primary Examiner—John D. Yasko
Attorney, Agent, or Firm—Gerstman, Ellis & McMillin, Ltd.

[57] ABSTRACT

A valved connector for a device for penetrating the arterial system of a patient. The connector comprises a tubular housing having a bore, plus a first valve for controlling back leakage through the tubular housing bore. The first valve is adjustably openable and closable to permit an elongated member to pass through the lumen of the first valve and bore of the housing, with the first valve providing selectively controllable sealing about the elongated member. A second valve is carried, typically proximal of the first valve. The second valve comprises a slit, resilient partition permitting the elongated member to pass through the slit partition with added sealing. Thus, back leakage through the housing can be controlled by the second valve when the first valve is opened, so that the elongated member passing through the connector can be easily moved by releasing the first valve without significant back leakage, so that the elongated member may be easily moved through the connector, but may be strongly sealed at any desired time.

12 Claims, 1 Drawing Sheet

DOUBLE SEAL HEMOSTASIS CONNECTOR

BACKGROUND OF THE INVENTION

Hemostasis connectors are well known in various surgical procedures, being used for access to the arterial system of a patient in angioplasty and angiography procedures. Also, hemostasis connectors may be used in conjunction with atherectomy procedures, the administration of laser catheters to the arterial system, and the like.

Typically, an elongated member such as an atherectomy device, a laser catheter, or a PTCA balloon catheter passes through a tubular hemostasis connector which carries a hemostasis seal, through which the elongated member penetrates within the tubular connector. In some circumstances, the hemostasis seal may be a slit elastomeric partition, which permits the passage of a catheter or the like, but seals around it, and also seals in the absence of the elongated member to prevent back bleeding due to arterial or flushing pressure.

In other hemostasis connectors, the hemostasis seal device is of the Tuohy-Borst type, in which a valve or gasket opening is variably adjusted in diameter. The Tuohy-Borst type of structure comprises a tubular, elastomeric member having a central opening therethrough, and a screw threaded member which can be advanced to adjustably pressurize the elastomeric member, with the result that the central opening is of variable size, depending upon the degree of pressurization. Thus, in this latter type of device, a catheter or the like may pass through the adjustable valve opening, with the diameter of the opening then being reduced or clamped down onto the catheter for a tight hemostasis seal. Such adjustable hemostasis valves are often used for larger catheters and other elongated members of a size of typically French 9 or larger, such as arthrectomy devices, laser catheters, and the like.

However, as a disadvantage of the adjustable, variable hemostasis connector valves, while they seal tightly against back bleeding due to arterial pressure, flushing, or the like, a catheter or other device passing through the valve is not advanced or retracted with ease while the adjustable valve is providing such good sealing. Thus, typically, the surgeon is forced to release the sealing pressure on the catheter passing through the adjustable valve for adjustment of the position of the catheter, sliding it through the valve to a different position. During this period of time, substantial back bleeding or other leakage can take place.

In accordance with this invention, a hemostasis connector is provided which is capable of adjustable valved sealing of a catheter or other elongated member passing therethrough, but when the sealing is released to facilitate movement of the catheter through the valve, back leakage is greatly suppressed. Thus, a valve is provided in which substantial pressures of flushing of x-ray contrast fluid or the like can be utilized without back leakage or back bleeding, but the device readily permits the sliding adjustment of the catheters, atherectomy devices, and the like passing through it.

DESCRIPTION OF THE INVENTION

By this invention, a valve connector is provided for a device for penetrating the arterial system of a patient. The device comprises a tubular housing having a bore, and first valve for controlling back leakage through the tubular housing bore. The first valve is adjustably openable and closable to permit an elongated member to pass through the bore of the first valve and the housing, with the first valve providing selectively controllable sealing about the elongated member.

A second valve is also provided, being carried proximal of the first valve on the housing. The second valve comprises a slit, resilient partition which permits the elongated member to pass through the partition for added sealing.

As the result of this, back leakage through the housing can be controlled even when the first valve is opened. However, for especially heavy back pressures as in flushing, the adjustable first valve can be tightened to further suppress back leakage, but it may be loosened for movement of the elongated member through the valved connector of this invention, with greatly reduced back leakage.

Preferably, a branch conduit connects with the tubular housing distal to the first valve. Also, the first valve preferably comprises a resilient, tubular valve member having a lumen that communicates with the bore of the tubular housing. A rotatable, screw-threaded pressure member may be present to adjustably compress the resilient valve member to control the diameter of the bore.

In this circumstance, it may be preferred for the second valve to be carried by the rotatable pressure member, which pressure member defines an aperture which is aligned with the bore, and the lumen of the first valve, to permit passage of the elongated member.

It is also desirable for the connector of this invention to carry, on its distal end, a rotatable luer lock member, to permit connection of the hemostasis connector to a guiding catheter or catheter introducer, which may be emplaced into the arterial system of the patient. As stated above, the valve connectors of this invention find particular usefulness with larger diameter catheters which are more likely to exhibit significant back leakage, so that the improved sealing characteristics of the device of this invention provide significant advantage.

DESCRIPTION OF SPECIFIC EMBODIMENTS

Figure 1:
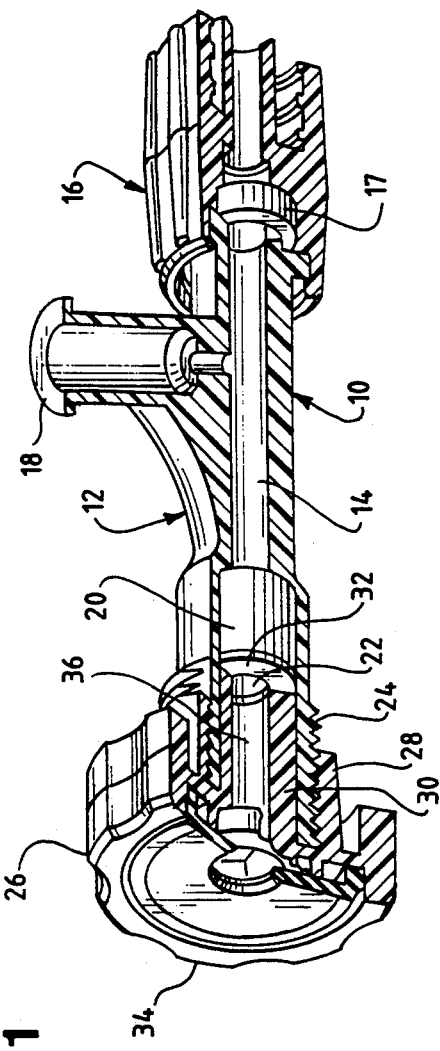
FIG. 1 is a perspective view, with portions broken away, of the valved connector in accordance with this invention.
Figure 2:
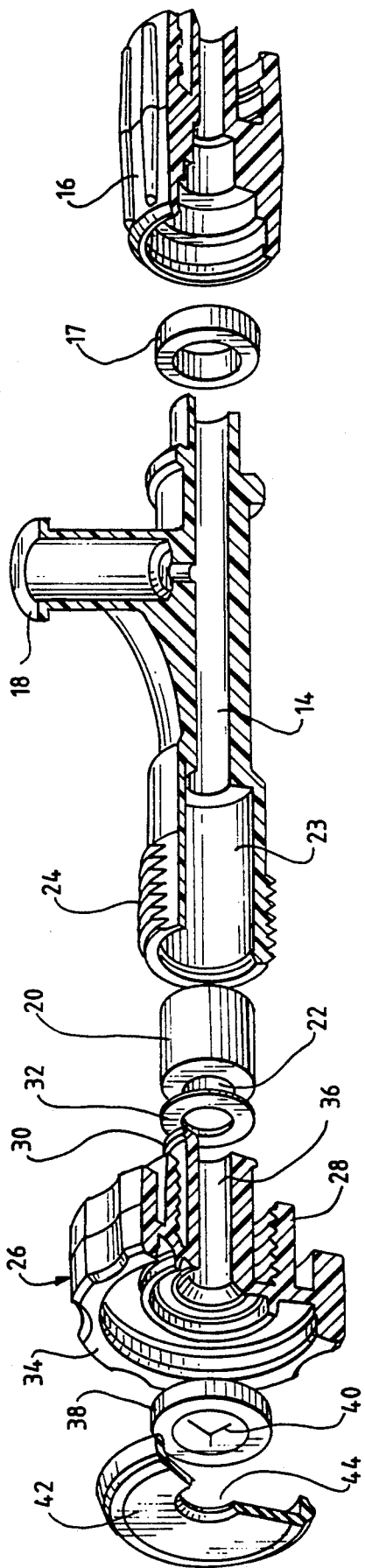
FIG. 2 is an exploded, perspective view, with portions broken away, of the valved connector of FIG. 1.

Referring to the drawings, a branched connector 10 having hemostasis characteristics is disclosed. Connector 10 comprises a tubular housing 12 defining a bore 14 that extends from end to end thereof. At the distal end of connector 10, a conventional luer lock connector 16 is provided, for connection in the conventional manner with a guiding catheter, or any other suitable device. Thus, the connector of FIGS. 1 and 2 can be applied when and as needed to a guiding catheter which already will have been implanted in the patient, if the guiding catheter carries an appropriate connector.

Branch conduit 18 is also provided, connecting with the bore 14 of the tubular housing at a position that is distal to the valves thereof. Branch conduit 18 may be used to provide flushing to the system from a separate, connected source of flush solution, and may terminate with a conventional female luer connector or the like.

First valve member 20 is provided within housing 12, with valve member 20 comprising a resilient tubular member defining a lumen 22 therethrough, which bore is aligned with bore 14 of the housing. First valve member 20 resides in an enlargement 23 in bore 14, as shown.

At the proximal end of housing 12 is an outwardly facing screw thread 24 upon which is carried a rotatable, screw threaded pressure member 26. Pressure member 26 defines an internally threaded sleeve 28 which rotates on screw threads 24, plus an integral, inner sleeve 30, which presses through washer 32 against tubular valve member 20. Screw threaded pressure member 26 also carries an integral handle 34 to facilitate manual rotation, and further defines a lumen 36 that communicates with bore 14 and lumen 22.

Thus, as one manually rotates handle 34 to advance pressure member 26 distally in its screw threaded relation, sleeve 30 presses washer 32 against resilient tubular valve member 20, which compresses the valve member and causes bore 22 to constrict. Thus, if a guiding catheter, for example, is passing through valved connector 10, tubular valve member 20 can be collapsed down upon it by turning handle 34, providing a strong seal against the back flushing of blood or other fluids, to prevent excessive proximal leakage through lumen 36.

Alternatively, handle 34 may be loosened to cause tubular valve member 20 to expand and to release the seal within bore 22. In this condition, while the sealing is less, a catheter or the like may be moved within bore 14 for advancement or retraction.

In accordance with this invention, rotatable pressure member 26 carries a second valve 38 in a position proximal to that of the first valve, comprising tubular valve member 20 and inner sleeve 30. Second valve 38 comprises a typically-known slit elastomeric partition defining a slit 40 extending therethrough, which permits an elongated member such as a guiding catheter to pass through second valve 38 with added sealing against back bleeding or other fluid leakage. Particular designs of such partitions 38 are available in the prior art. A preferred design for such a slit partition is disclosed in Hillstead U.S. Pat. No. 4,895,565.

Second valve partition 38 is held in a position of alignment with bore 14 and lumens 22, 36 by retention plate 42, which has a central aperture to permit access to second valve 38 and the respective bores and apertures, and which may be peripherally sealed to handle 34.

Accordingly, the device of this invention may be attached by its male luer connector 16 to a guiding catheter. Alternatively, the device may be permanently attached to the proximal end of such a catheter or the like. Then, an atherectomy catheter for example, typically having a French size above 9, may be passed into the guiding catheter through aperture 44, slit second valve 38, lumens 36 and 22, and bore 14, to extend through the entire length of connector 10 and through the attached guiding catheter as well.

When increased back pressures are encountered due to a high flush pressure through side port 18 or because of high arterial back pressures, handle 34 may be rotated to longitudinally compress first valve member 20, so that lumen 22 collapses down on the guiding catheter carried therein, promoting sealing against back leakage. However, when it is desired to advance or retract the guiding catheter, one can release the pressure of member 20 against the guiding catheter by the rotation of handle 34 in the other direction. Nevertheless, back leakage remains controlled by the constant presence and sealing characteristics of second valve member 38. Thus the device of this invention exhibits the advantages of excellent sealing against relatively high back pressures, while also being capable of easy advancement and retraction of the elongated member passing through connector 10, simply by manual rotation of handle 34 to achieve the conditions desired.

If desired, a third branched arm may be provided to connector 10 for use as a vent, and that branching arm may carry a valve system 20, 36 if desired, controlled by a screw-threaded pressure member 36 and further including another second valve member 38.

The above has been offered for illustrative purposes only, and is not intended to limit the scope of the invention of this application, which is as defined in the claims below.

That which is claimed is:

1. A valved connector for a device for penetrating the arterial system of a patient, which comprises:
a tubular housing having a bore; a first valve for controlling back leakage through said tubular housing bore, said first valve being adjustably openable and closable to permit an elongated member to pass through the bore of said first valve while providing selectively controllable sealing about said elongated member; and a second valve carried proximal of said first valve, said second valve comprising a slit, resilient partition permitting said elongated member to pass through said partition with added sealing, whereby back leakage through said housing can be controlled when said first valve is opened.

2. The connector of claim 1 in which a branch conduit connects with said tubular housing distal to said first valve.

3. The connector of claim 1 in which said first valve comprises a resilient, tubular valve member having a lumen that communicates with said bore, and a rotatable, screw-threaded pressure member to adjustably compress said resilient valve member to control the diameter of said lumen.

4. The connector of claim 1 which carries on its distal end a rotatable luer lock connector.

5. The connector of claim 1, attached to the proximal end of an elongated member having a size of at least French 9.

6. A valve connector for a device for penetrating the arterial system of a patient, which comprises:
a tubular housing having a bore; a first valve for controlling back leakage through said tubular housing bore, said first valve defining a lumen and being adjustably openable and closable to permit an elongated member to pass through the lumen of said first valve and the bore of said housing, with said first valve providing selectively controllable sealing about said elongated member; and a second valve carried by a rotatable, screw-threaded pressure member in a position proximal of said first valve, said second valve comprising a slit, resilient partition permitting said elongated member to pass through said partition with added sealing, whereby back leakage through said housing can be controlled when said first valve is opened, said first valve comprising a resilient, tubular valve member having said lumen that communicates with said bore, said rotatable, screw-threaded pressure member being positioned to adjustably compress said resilient valve member to control the diameter of said lumen; and a branch conduit connecting with said tubular housing distal to said first valve.

7. The connector of claim 6, attached to the proximal end of a catheter having a size of at least French 9.

8. The connector of claim 7 which carries on its distal end a rotatable luer lock member.

9. A valved connector for a device for penetrating the arterial system of a patient, which comprises:

a tubular housing having a bore; a first valve for controlling back leakage through said tubular housing bore, said first valve being adjustably openable and closable to permit an elongated member to pass through the bore of said first valve while providing selectively controllably sealing about said elongated member, said first valve comprising a resilient, tubular valve member having a lumen that communicates with said bore, and a rotatable, screw-threaded pressure member to adjustably compress said resilient valve member to control the diameter of said lumen; and a second valve carried by said rotatable pressure member proximal of said first valve, said second valve comprising a slit, resilient partition permitting said elongated member to pass through said partition with added sealing, whereby back leakage through said housing can be controlled when said first valve is opened.

10. The connector of claim 9 which carries on its distal end a rotatable luer lock connector.

11. The connector of claim 10 in which a branch conduit connects with said tubular housing distal to said first valve.

12. The connector of claim 11, attached to the proximal end of a catheter having a size of at least French 9.

* * * * *